US009550747B2

United States Patent
Zhu et al.

(10) Patent No.: US 9,550,747 B2
(45) Date of Patent: Jan. 24, 2017

(54) DAPAGLIFLOZIN CRYSTALLINE FORM AND PREPARATION METHOD THEREOF

(71) Applicant: Jiangsu Hansoh Pharmaceutical Group Co., Ltd., Lianyungang, Jiangsu (CN)

(72) Inventors: Xifeng Zhu, Jiangsu (CN); Xiaobi Li, Jiangsu (CN); Tiancheng Zhang, Jiangsu (CN); Fuping Yuan, Jiangsu (CN)

(73) Assignee: Jiangsu Hansoh Pharmaceutical Group Co., Ltd., Lianyungang, Jiangsu (CN)

( * ) Notice: Subject to any disclaimer, the term of this patent is extended or adjusted under 35 U.S.C. 154(b) by 0 days.

(21) Appl. No.: 15/117,533

(22) PCT Filed: Jan. 19, 2015

(86) PCT No.: PCT/CN2015/071009
§ 371 (c)(1),
(2) Date: Aug. 9, 2016

(87) PCT Pub. No.: WO2015/117538
PCT Pub. Date: Aug. 13, 2015

(65) Prior Publication Data
US 2016/0347731 A1 Dec. 1, 2016

(30) Foreign Application Priority Data

Feb. 10, 2014 (CN) .......................... 2014 1 0046371

(51) Int. Cl.
C07H 7/04 (2006.01)
C07H 1/06 (2006.01)
C07D 309/10 (2006.01)

(52) U.S. Cl.
CPC .............. *C07D 309/10* (2013.01); *C07H 1/06* (2013.01); *C07H 7/04* (2013.01); C07B 2200/13 (2013.01)

(58) Field of Classification Search
None
See application file for complete search history.

(56) References Cited

U.S. PATENT DOCUMENTS

| 7,919,598 B2 * | 4/2011 | Gougoutas | C07H 7/04 536/1.11 |
| 9,394,328 B2 * | 7/2016 | Blatter | C07D 309/10 |
| 2013/0046088 A1 | 2/2013 | Liou et al. | |
| 2014/0249098 A1 * | 9/2014 | Puskas | A61K 31/70 514/35 |

FOREIGN PATENT DOCUMENTS

| CN | 101479287 A | 7/2009 |
| WO | 2013079501 A1 | 6/2013 |

OTHER PUBLICATIONS

Int'l Search Report issued Mar. 25, 2015 in Int'l Application No. PCT/CN2015/071009.

* cited by examiner

*Primary Examiner* — Traviss C McIntosh, III
(74) *Attorney, Agent, or Firm* — Panitch Schwarze Belisario & Nadel LLP

(57) ABSTRACT

The present invention relates to a new crystalline form of dapagliflozin represented by formula (I). The crystalline form has a characteristic absorption peak at about 4.318 (20.45) in an X-ray powder diffraction pattern shown by angle 2 theta and interplanar spacing (value d). It can be prepared by dissolving dapagliflozin in good organic solvents, adding poor solvents, stirring to crystallization, filtering and drying. The new crystalline form of dapagliflozin of the present invention has the following superior features: good solubility, low hygroscopicity, high stability and good preparation reproducibility.

12 Claims, 2 Drawing Sheets

DAPAGLIFLOZIN CRYSTALLINE FORM AND PREPARATION METHOD THEREOF

CROSS-REFERENCE TO RELATED APPLICATION

This application is a Section 371 of International Application No. PCT/CN2015/071009, filed Jan. 19, 2015, which was published in the Chinese language on Aug. 13, 2015, under International Publication No. WO 2015/117538 A1, and the disclosure of which is incorporated herein by reference.

FIELD OF THE INVENTION

The present invention belongs to the field of polymorphism drug preparation, and specifically relates to a new crystalline form of dapagliflozin and a preparation method thereof.

BACKGROUND OF THE INVENTION

Dapagliflozin, developed by Bristol-Myers Squibb and AstraZeneca, is used for the treatment of Type II diabetes ($Na^+$-glucose cotransporter-2 (SGLT-2) inhibitors).

Bristol-Myers Squibb and AstraZeneca submitted an application to the European Medicines Agency (EMA) in December 2010, and the European Committee of Human Medicinal Products approved dapagliflozin for the treatment of type II diabetes in April 2012.

Bristol-Myers Squibb and AstraZeneca also submitted an application to the Food and Drug Administration (FDA) in December 2010, and the FDA issued a response letter requiring Bristol-Myers Squibb and AstraZeneca to provide additional clinical data in January 2012.

The chemical name of dapagliflozin is 2-chloro-5-(β-D-glucopyranosyl-1-yl)-4'-ethoxy-diphenylmethane, and the chemical structure is as follows:

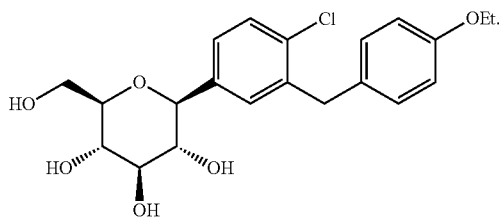 [SMILES: CCOc1ccc(Cc2cc([C@@H]3O[C@H](CO)[C@@H](O)[C@H](O)[C@H]3O)ccc2Cl)cc1]

Thus far, only 9 crystal forms of dapagliflozin are reported in its original patent (CN101479287), which are dapagliflozin solvates and amino acid complexes. The details are as follows:

| Crystal form | Description | Preparation method |
|---|---|---|
| Ia | Dapagliflozin (S)-propylene glycol monohydrate | To a solution of (S)-propylene glycol, water and dapagliflozin, cyclohexane and methyl tert-butyl ether are added and cooled to 5° C., then stirred to crystallization. |
| Ib | Dapagliflozin (R)-propylene glycol monohydrate | To a solution of (R)-propylene glycol, water and dapagliflozin, cyclohexane and methyl tert-butyl ether are added and cooled to 5° C., then stirred to crystallization. |
| Ic | Dapagliflozin Ethanol dihydrate | Dapagliflozin is dissolved in ethanol, diluted with water and cooled to −10 to −20° C., then stirred to crystallization. |
| Id | Dapagliflozin Ethylene glycol dihydrate | Dapagliflozin is dissolved in ethylene glycol aqueous solution and crystal Ia is added, then stirred to crystallization. |
| Ie | Dapagliflozin Ethylene glycol dihydrate | Dapagliflozin is dissolved in ethylene glycol aqueous solution and crystal Ic is added, then stirred to crystallization. |
| Ih | Dapagliflozin-di-L-proline complex | L-proline is dissolved in water under heating. Isopropanol and a solution of dapagliflozin in isopropanol are added in order to crystallize. |
| Ii | Dapagliflozin-L-proline complex | L-proline is dissolved in an ethanol/water mixture under heating. A solution of dapagliflozin in ethanol is added and cooled to −20° C. to crystallization. |
| Ij | Dapagliflozin-L-proline semihydrate | L-proline and dapagliflozin are heated to dissolve in 97% ethanol/water mixture and then cooled to −20° C. before adding crystal Ii, then stirred to obtain white solid Ij. |
| Ik | Dapagliflozin-L-phenylalanine complex | L-phenylalanine is heated to dissolve in water and a solution of dapagliflozin in ethanol is added to obtain complex Ik. |

SUMMARY OF THE INVENTION

The object of the present invention is to provide a novel and unique crystal form.

The new crystalline form of dapagliflozin of formula (I) according to the present invention has an X-ray powder diffraction (XRPD) as shown in FIG. 1.

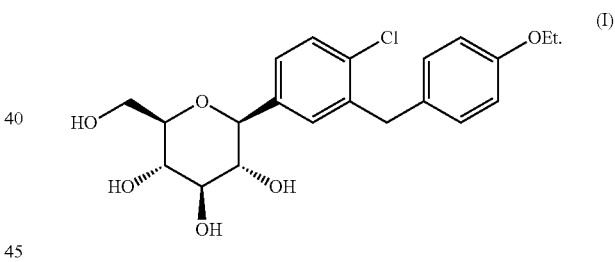

The crystalline form has a characteristic absorption peak at about 4.318 (20.45) in XRPD represented by 2θ degrees and spacing (d value).

Another object of the present invention is to provide a method for preparing the new crystalline form of dapagliflozin according to the present invention comprising obtaining the crystalline form of dapagliflozin in organic solvent at a temperature of 0° C. to 30° C.

In a preferred embodiment, dapagliflozin is dissolved in a good organic solvent and then added with a poor solvent, and then the mixture is stirred to crystallization. The precipitate is filtered and dried at a temperature of 0 to 30° C. to give the intended crystal form.

In another preferred embodiment, the good organic solvent is selected from ether solvents, preferably diethyl ether or methyl t-butyl ether.

In another preferred embodiment, the poor organic solvent is selected from alkane solvents, preferably n-hexane or n-heptane.

Preferably, the reaction temperature is in a range of 10 to 20° C.

Preferably, the stirring duration for crystallization is in a range of 1.5 to 2 hours.

Preferably, the drying temperature is in a range of 10 to 30° C.

Preferably, the drying is under vacuum.

Moreover, the method for preparing dapagliflozin is as follows: dapagliflozin is dissolved in a good solvent and then added with a poor solvent; the mixture is stirred to crystallization; and the precipitate is filtered and dried to give a crystal form of dapagliflozin.

Moreover, the detailed steps are as follows: dapagliflozin is dissolved in a good organic solvent and then added with a poor solvent; the mixture is then stirred for 1.5 to 2 hours at 30° C.; and the precipitate is filtered and dried under vacuum at 0 to 30° C. to give a crystal form of dapagliflozin.

The present invention provides a new process for preparing a dapagliflozin crystal. The process has the advantages of good solubility, low hygroscopicity, stable process, easy operation, high yield and good reproducibility, and the resulting crystal is stable and suitable for medical use.

DETAILED DESCRIPTION OF THE INVENTION

Example 1

Figure 1:
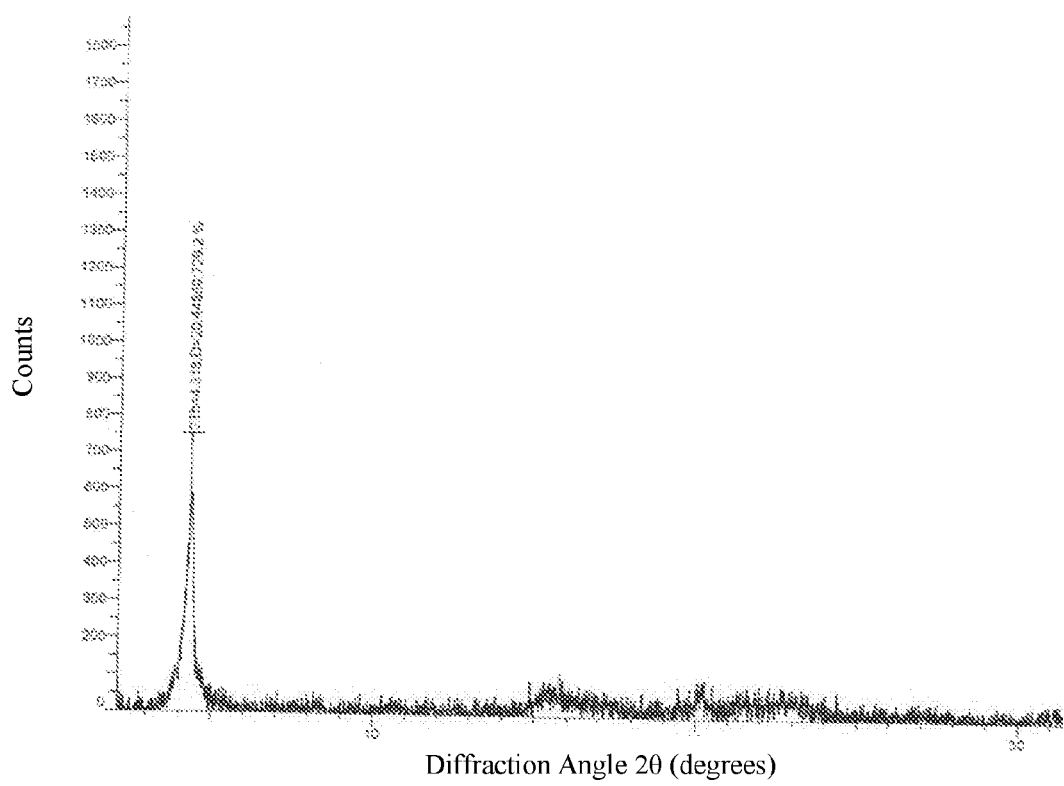
FIG. 1 shows an X-ray powder diffraction of a new crystalline form of dapagliflozin.

Preparation of a New Crystal Form of Dapagliflozin 0.5 g of dapagliflozin was weighed and added with 4.5 mL of diethyl ether. The mixture was stirred until it was clearly dissolved, and then added with N-hexane (20 mL). There was a white oil adhered to the flask-wall. Stirring was continued for 1.5 h. The resulting precipitate was filtered and dried to give 0.42 g product (white power solid). The XRPD of the product was consistent with FIG. 1.

Example 2

Preparation of a New Crystal Form of Dapagliflozin 0.5 g of dapagliflozin was weighed and added with 3 mL of diethyl ether. The mixture was stirred until it was clearly dissolved, and then added with N-hexane (10 mL). There was a white oil adhered to the flask-wall. Stirring was continued for 2 h. The resulting precipitate was filtered and dried to give 0.33 g product (white power solid). The XRPD of the product was consistent with FIG. 1.

Example 3

Preparation of a New Crystal Form of Dapagliflozin 0.5 g of dapagliflozin was weighed and added with 3 mL of methyl tert-butyl ether. The mixture was stirred until it was clearly dissolved, and then added with N-heptane (10 mL). There was a white oil adhered to the flask-wall. Stirring was continued for 2 h. The resulting precipitate was filtered and dried to give 0.35 g product (white power solid). The XRPD of the product was consistent with FIG. 1.

Experimental Example 1

Stability Study

1. Accelerated Test

The crystal resulting from Example 1 was placed under acceleration conditions for 6 months. The quality indicators of the sample did not change significantly and were in accordance with the quality standard. The range of a maximum single impurity was from 0.02% to 0.05%. The range of total impurity was from 0.10% to 0.14%. The total content ranged from 99.3% to 99.7%. Specific data are shown in Table 1.

Conditions: 30° C.±2° C./RH 65%±5%

Package: Two layers of low density polyethylene bag for medicinal use were sealed by hot-melt respectively, and desiccant was added. The bag was sealed and packaged with a pharmaceutical composite film bag of polyester/aluminum/polyamide/cast polypropylene.

TABLE 1

Results of Accelerated Test

| Items | 0 | 1 Month | 2 Months | 3 Months | 6 Months |
|---|---|---|---|---|---|
| Appearance | off-white powder, odorless | off-white powder, odorless | off-white powder, odorless | off-white powder, odorless | off-white powder, odorless |
| Specific Rotation | +13.3° | +13.2° | +13.0° | +13.4° | +13.3° |
| HPLC Identification | accordance | accordance | accordance | accordance | accordance |
| Related Substances Maximum Single Impurity (%) | 0.04 | 0.03 | 0.03 | 0.03 | 0.03 |
| Total Impurity (%) | 0.11 | 0.10 | 0.11 | 0.10 | 0.13 |
| Clarity and Color of Ethanol Solution | clear and colorless | clear and colorless | clear and colorless | clear and colorless | clear and colorless |
| Moisture Content (%) | 0.76 | 0.82 | 0.81 | 0.77 | 0.81 |
| Total Content (%) | 99.4 | 99.6 | 99.7 | 99.3 | 99.5 |
| XRPD | accordance | accordance | accordance | accordance | accordance |

2. Long-Term Test

The crystal resulting from Example 1 was placed under acceleration conditions for 6 months. The quality indicators of the sample did not change significantly and were in accordance with the quality standard. The range of a maximum single impurity was from 0.02 to 0.05%. The range of total impurity was from 0.10% to 0.15%. The total content ranged from 99.3% to 99.7%. Specific data are shown in Table 2.

Conditions: 21° C.±2° C./RH 45%±5%

Package: Two layers of low density polyethylene bag for medicinal use were sealed by hot-melt respectively, and desiccant was added. The bag was sealed and packaged with a pharmaceutical composite film bag of polyester/aluminum/polyamide/cast polypropylene.

TABLE 2

Results of Long-Term Test

| Item | | 0 | 3 Months | 6 Months |
|---|---|---|---|---|
| Appearance | | off-white powder, odorless | off-white powder, odorless | off-white powder, odorless |
| Specific Rotation | | +13.3° | +13.1° | +12.9° |
| HPLC Identification | | accordance | accordance | accordance |
| Related Substances | Maximum Single Impurity (%) | 0.04 | 0.03 | 0.03 |
| | Total Impurity (%) | 0.11 | 0.11 | 0.13 |
| Clarity and Color of Ethanol Solution | | clear and colorless | clear and colorless | clear and colorless |
| Moisture Content (%) | | 0.76 | 0.77 | 0.80 |
| Total Content (%) | | 99.4 | 99.8 | 99.5 |
| XRPD | | accordance | accordance | accordance |

3. Stability Study of Crystal after Grinding or Pressing

Figure 2:
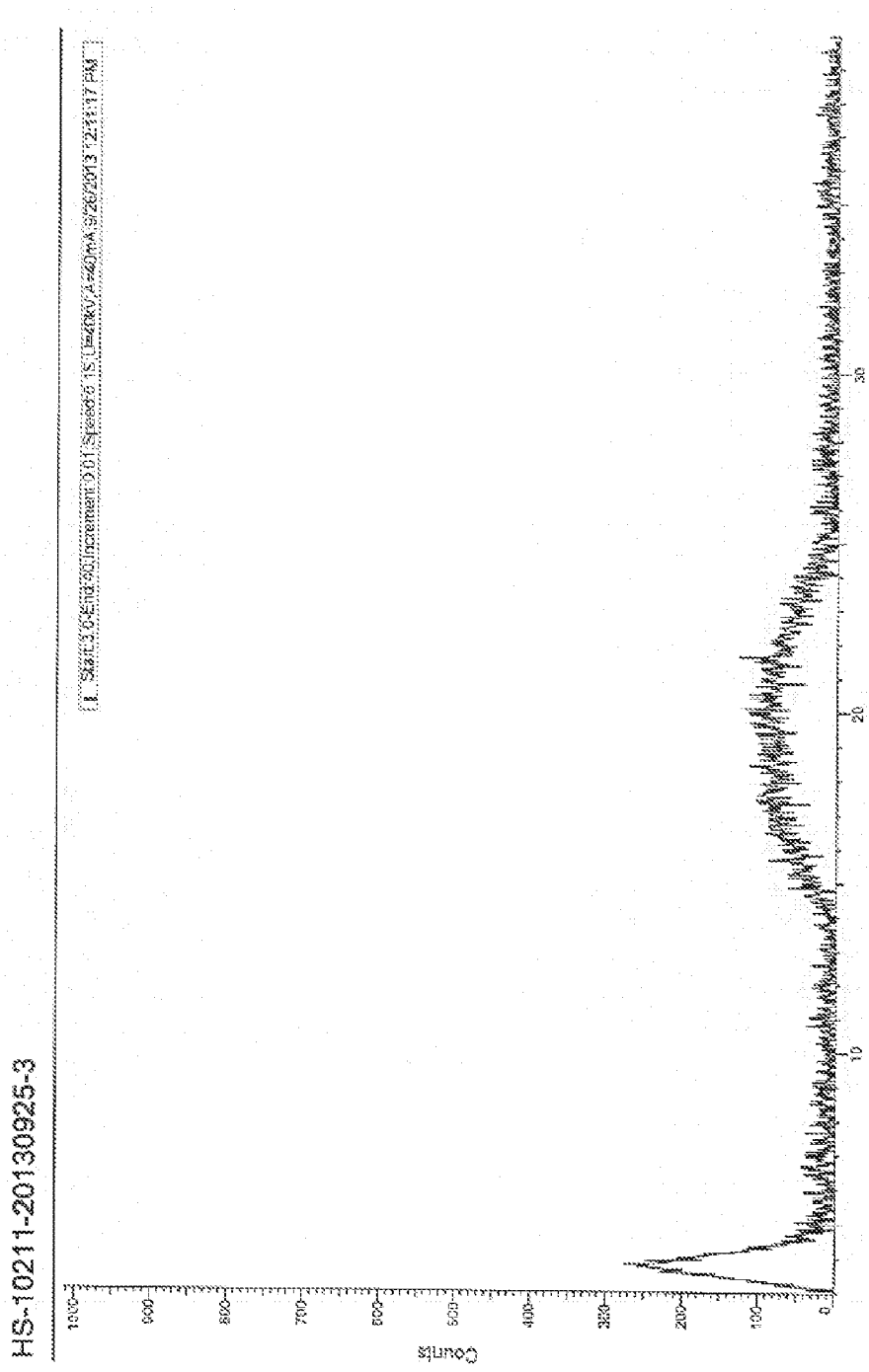
FIG. 2 shows an X-ray powder diffraction of a new crystalline form of dapagliflozin after pressing into a tablet.

It can be seen from FIG. 2 that there is no transformation of the crystal of the present invention after pressing into a tablet, which indicates that the crystal according to the present invention is stable. In the same test, the XRPD shows that grinding does not result in transformation of the crystal.

Experimental Example 2

Hygroscopicity Test

The crystal resulting from example 1 was sampled in the hygroscopicity test, and the results are shown in table 3.

TABLE 3

Results of Hygroscopicity Test

| Item | limitation | High humidity test 25° C./RH 75% (day) | | | High humidity test 25° C./RH 95% (day) | | |
|---|---|---|---|---|---|---|---|
| | | 0 | 5 | 10 | 0 | 5 | 10 |
| hygroscope | — | — | 4.83% | 4.84% | — | 6.09% | 6.71% |

What is claimed is:

1. A crystalline form of dapagliflozin represented by formula (I):

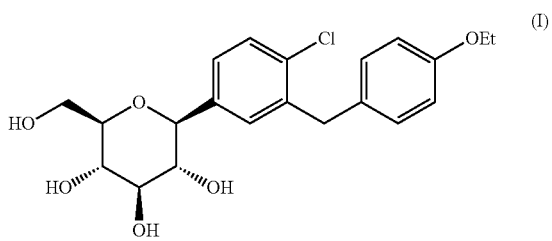 [SMILES: CCOc1ccc(Cc2cc([C@@H]3O[C@H](CO)[C@@H](O)[C@H](O)[C@H]3O)ccc2Cl)cc1]

the crystalline form having a characteristic X-ray powder diffraction (XRPD) peak at:

| Angle (2θ) | d-Value (Angstrom) |
|---|---|
| about 4.318 | about 20.45. |

2. A method for preparing the crystalline form of dapagliflozin represented by formula (I) according to claim 1, wherein the crystalline form of dapagliflozin is obtained in an organic solvent at a temperature of 0° C. to 30° C.

3. The method according to claim 2, wherein the method comprises:
(a) dissolving dapagliflozin in a good organic solvent;
(b) adding a poor solvent to the solution of dapagliflozin in the good solvent obtained in step (a), thereby producing a mixture;
(c) stirring the mixture to crystallization;
(d) filtering the precipitate from the mixture; and
(e) drying the filtered precipitate obtained in step (d) at a temperature of 0 to 30° C. to obtain the crystalline form.

4. The method according to claim 3, wherein the good organic solvent is selected from the group consisting of ether solvents.

5. The method according to claim 3, wherein the poor solvent is selected from the group consisting of alkane solvents.

6. The method according to claim 2, wherein the temperature is in a range of 10 to 20° C.

7. The method according to claim 3, wherein the mixture is stirred to crystallization in step (c) for a duration of 1.5 to 2 hours.

8. The method according to claim 3, wherein the filtered precipitate is dried at a temperature in a range of 10 to 30° C.

9. The method according to claim 3, wherein the drying is under vacuum.

10. The crystalline form of dapagliflozin according to claim 1, having a XRPD pattern as shown in FIG. 1.

11. The method according to claim 4, wherein the good organic solvent is diethyl ether or methyl t-butyl ether.

12. The method according to claim 5, wherein the alkane solvent is n-hexane or n-heptane.

* * * * *